(12) United States Patent
Lancaster et al.

(10) Patent No.: US 11,826,491 B2
(45) Date of Patent: Nov. 28, 2023

(54) COMPOSITIONS AND METHODS FOR IMPROVING CARDIAC FUNCTION

(71) Applicant: Arizona Board of Regents on Behalf of the University of Arizona, Tucson, AZ (US)

(72) Inventors: Jordan J. Lancaster, Tucson, AZ (US); Steven Goldman, Tucson, AZ (US); Jennifer W. Koevary, Tucson, AZ (US); Ikeotunye R. Chinyere, Tucson, AZ (US)

(73) Assignee: Arizona Board of Regents on Behalf of the University of Arizona, Tucson, AZ (US)

(*) Notice: Subject to any disclaimer, the term of this patent is extended or adjusted under 35 U.S.C. 154(b) by 874 days.

(21) Appl. No.: 16/629,070

(22) PCT Filed: Jul. 7, 2018

(86) PCT No.: PCT/US2018/041161
§ 371 (c)(1),
(2) Date: Jan. 7, 2020

(87) PCT Pub. No.: WO2019/010464
PCT Pub. Date: Jan. 10, 2019

(65) Prior Publication Data
US 2020/0171206 A1    Jun. 4, 2020

Related U.S. Application Data

(60) Provisional application No. 62/530,015, filed on Jul. 7, 2017.

(51) Int. Cl.
| | | |
|---|---|---|
| *A61L 27/38* | (2006.01) | |
| *A61P 9/00* | (2006.01) | |
| *A61K 35/34* | (2015.01) | |
| *A61L 27/54* | (2006.01) | |
| *A61L 27/56* | (2006.01) | |
| *A61L 27/58* | (2006.01) | |
| *A61K 38/22* | (2006.01) | |
| *A61K 38/18* | (2006.01) | |
| *A61K 38/00* | (2006.01) | |

(52) U.S. Cl.
CPC .......... *A61L 27/3834* (2013.01); *A61K 35/34* (2013.01); *A61K 38/00* (2013.01); *A61K 38/1833* (2013.01); *A61K 38/2292* (2013.01); *A61L 27/3826* (2013.01); *A61L 27/3886* (2013.01); *A61L 27/54* (2013.01); *A61L 27/56* (2013.01); *A61L 27/58* (2013.01); *A61P 9/00* (2018.01); *A61L 2300/414* (2013.01); *A61L 2430/20* (2013.01)

(58) Field of Classification Search
None
See application file for complete search history.

(56) References Cited

U.S. PATENT DOCUMENTS

| | | |
|---|---|---|
| 2008/0089874 A1 | 4/2008 | Li et al. |
| 2009/0169521 A1 | 7/2009 | Levenberg et al. |
| 2015/0368618 A1 | 12/2015 | Nadal-Ginard |
| 2016/0250384 A1 | 9/2016 | Lancaster |

FOREIGN PATENT DOCUMENTS

| | | |
|---|---|---|
| WO | WO 2003/094855 | 11/2003 |
| WO | WO 2013/028968 | 2/2013 |
| WO | WO 2015/054383 | 4/2015 |
| WO | WO 2015/081226 | 6/2015 |
| WO | WO 2019/099863 | 5/2019 |
| WO | WO 2019/222578 | 11/2019 |

OTHER PUBLICATIONS

Psaltis et al, Circulation Research, 2015, vol. 116, pp. 1392-1412. (Year: 2015).*
Zhang et al, Cell Research, 2011, vol. 21, pp. 579-587. (Year: 2011).*
EP Search Report, EP PatentApplication No. 188277776, dated Mar. 3, 2021, 14 pages.
Ye, L. et al. Patching the Heart: Cardiac Repair From Within and Outside, Circulation Research. 2013;113:922-932.
Shiba Yuji et al. Cardiac Applications for Human Pluripotent Stem Cells, Current Pharmaceutical Design, vol. 15, No. 24, 2009, pp. 2791-2806(16).
Lancaster, J. et al. An electrically coupled tissue-engineered cardiomyocyte scaffold improves cardiac function in rats with chronic heart failure, J Heart Lung Transplant. Apr. 2014;33(4):438-45.
Lancaster, J. et al. Construction of a Spontaneously Contracting Biologically Active Cardiomyocyte Scaffold, Journal of Cardial Failure, Churchill Livingstone, Naperville, IL, US, vol. 15, No. 6, Aug. 1, 2009, pp. S44-S45.
Jung, G. hiPSC Modeling of Inherited Cardiomyopathies, Curr Treat Options Cardiovasc Med. Jul. 2014;16(7):320.
Kreutziger, K. et al. Engineered Human Cardiac Tissue, Pediatric Cardiology vol. 32, No. 3, pp. 334-341(2011).
Madden, LR et al. Proangiogenic scaffolds as functional templates for cardiac tissue engineering, Proc Natl Acad Sci U S A. Aug. 24, 2010;107(34): 15211-6.
Radisic M. et al. Functional assembly of engineered myocardium by electrical stimulation of cardiac myocytes cultured on scaffolds, Proc Natl Acad Sci U S A. Dec. 28, 2004;101(52):18129-34.

(Continued)

*Primary Examiner* — Allison M Fox
(74) *Attorney, Agent, or Firm* — Casimir Jones, S.C.; Robert A. Goetz

(57) ABSTRACT

The present invention provides compositions and methods for improving cardiac function. Specifically, the present invention provides compositions and methods for treating a subject having a disorder or condition associated with aberrant cardiac tissue function, comprising contacting a patient having a disorder or condition associated with aberrant cardiac tissue function with a construct, or a construct associated with therapeutic cells, or a construct associated with fibroblast cells and therapeutic cells.

11 Claims, 4 Drawing Sheets

(56) References Cited

OTHER PUBLICATIONS

Kawaguchi, N. et al. 3D-Culture System for Heart Regeneration and Cardiac Medicine, BioMed Research International 2013, pp. 1-6.
Shachar, M. et al. The effect of immobilized RGD peptide in alginate scaffolds on cardiac tissue engineering, Acta Biomater. Jan. 2011;7(1):152-62.
Wang, Wei Eric et al. Potential of cardiac stem/progenitor cells and induced pluripotent stem cells for cardiac repair in ischaemic heart disease, Clin Sci (Lond). Oct. 2013;125(7):319-27.
Lundy, S. et al. Structural and functional maturation of cardiomyocytes derived from human pluripotent stem cells, Stem Cells Dev. Jul. 15, 2013;22(14):1991-2002.
Dar A. et al. Optimization of cardiac cell seeding and distribution in 3D porous alginate scaffolds, Biotechnol Bioeng. Nov. 5, 2002;80(3):305-12.
Radisic M. et al. Pre-treatment of synthetic elastomeric scaffolds by cardiac fibroblasts improves engineered heart tissue, J Biomed Mater Res A. Sep. 2008;86(3):713-24.
International Search Report & Written Opinion, Int'l Patent Application No. PCT/US2018/041161, dated Jul. 7, 2018, 8 pages.

\* cited by examiner

COMPOSITIONS AND METHODS FOR IMPROVING CARDIAC FUNCTION

CROSS REFERENCE TO RELATED APPLICATIONS

This application is a U.S. 371 national phase entry of International Patent Application No. PCT/US2018/041161, filed Jul. 7, 2018, which claims priority to and the benefit of U.S. Provisional Application No. 62/530,015, filed Jul. 7, 2017, which are hereby incorporated by reference in their entireties.

FIELD OF THE INVENTION

The present invention provides compositions and methods for improving cardiac function. Specifically, the present invention provides compositions and methods for treating a subject having a disorder or condition associated with aberrant cardiac tissue function, comprising contacting a patient having a disorder or condition associated with aberrant cardiac tissue function with a construct, or a construct associated with therapeutic cells.

BACKGROUND

Heart rhythm problems (arrhythmias) occur when there is a malfunction in the electrical impulses that coordinate the heartbeat. More than 4 million Americans, most over age 60, experience heart arrhythmias that may cause dangerous symptoms, which may include shortness of breath, fainting, loss of heart function, loss of breathing, and loss of consciousness that can leads to death. About 2.2 million Americans experience atrial fibrillation, making it the most common medically significant arrhythmia. VT is a rapid, regular heartbeat originating from a site in one of the ventricles instead of from the sinus node in the right atrium. Frequently, the site is an area of scar tissue in the heart's muscular wall caused by damage from a heart attack. Congenital conditions, coronary artery disease and cardiomyopathy (frequently resulting from heart attack) are risk factors for arrhythmias. Twenty-six million people worldwide are diagnosed with chronic heart failure (CHF). With only 5,000 heart transplants performed annually, the prognosis for these individuals is poor and new therapeutic options are needed. Patients with an Ejection Fraction less than 35% are commonly implanted with an implantable cardioverter-defibrillator (ICD).

Treatment for arrhythmias focuses on trying to control heart rate within a normal range and treating the conditions causing the abnormal beats. Treatments may include medications, vagal maneuvers, cardioversion (shock), or catheter ablation. Current treatments are not always able to treat the root of the disease and arrhythmias can continue to occur following treatment. Catheter ablation, for example, does not always target the correct location in the heart, or the arrhythmia can occur in a different place after one area is treated.

The present invention addresses this need.

SUMMARY

Experiments conducted during the course of developing embodiments for the present invention investigated the use of engineered grafts for improving cardiac function. Such experiments examined comparatively the therapeutic benefits of grafts alone, grafts engineered with different therapeutic cells populations, or grafts engineered with different therapeutic cell populations and fibroblast cells. Improved cardiac function outcome was demonstrated for each of grafts alone, grafts engineered with different therapeutic cells populations, or grafts engineered with different therapeutic cell populations and fibroblast cells.

Accordingly, the present invention provides compositions and methods for improving cardiac function. Specifically, the present invention provides compositions and methods for treating a subject having a disorder or condition associated with aberrant cardiac tissue function, comprising contacting a patient having a disorder or condition associated with aberrant cardiac tissue function with a construct, or a construct associated with therapeutic cells.

In certain embodiments, the present invention provides methods for treating a subject having a disorder or condition associated with aberrant cardiac tissue function. The present invention is not limited to specific techniques related to the provided methods of treatment.

In some embodiments, such methods comprise contacting a patient having a disorder or condition associated with aberrant cardiac tissue function with a scaffold. In some embodiments, the scaffold is a substrate comprising a biocompatible, non-living material.

Such methods are not limited to treating a particular disorder or condition associated with aberrant cardiac tissue function. In some embodiments, the disorder or condition associated with aberrant cardiac tissue function is a cardiac arrhythmia. In some embodiments, the cardiac arrhythmia is selected from the group consisting of tachycardia, bradycardia, ventricular tachycardia, ventricular fibrillation, arrhythmias generated from the upper chambers of the heart such as any supraventricular tacchycardia such as atrial fibrillation, and diseases of the atrioventricular nodal tissue such as complete heart block. In some embodiments, the cardiac arrhythmia is ventricular tachycardia.

In some embodiments, a therapeutic cell population such as a fibroblast cell population is associated with the scaffold. In some embodiments, an additional therapeutic cell population is associated with the scaffold. In some embodiments, several (i.e. more than two) therapeutic cell populations are associated with the scaffold. In some embodiments, the therapeutic cell population is adhered to the scaffold. In some embodiments the cells may be from one donor, or two different donors or multiple different donors.

In some embodiments, the therapeutic cell population is mesoderm lineage cells such as cardiac cells, or progenitors thereof, or stem cells, or cells derived from stem cells, or multiple types of cells. In some embodiments, the therapeutic cell population is a ventricular myocyte (VM) population, an atrial myocyte population, a nodal myocyte population, a heterogeneous cardiac myocyte (hetCM), a cardiac progenitor population a stem cell population, or combinations thereof. In some embodiments, the hetCM comprise a mixture of ventricular, atrial, and nodal cardiomyocytes. In some embodiments, the hetCM comprise 50%-90% ventricular cardiomyocytes, and 10%-50% atrial and nodal cardiomyocytes, or about 60% ventricular, and about 40% atrial and nodal cardiomyocytes. In some embodiments, the therapeutic cell population includes hiPSC-derived heterogeneous cardiac myocytes (hetCM) and/or ventricular pure myocytes (VM). In some embodiments, the therapeutic cell population is derived from hiPSC (human induced pluripotent stem cell) or embryonic stem cells or primary cells, or derived from primary cells. In some embodiments, the therapeutic cells comprise progenitor cardiac cells, terminally differentiated cardiac cells, or combinations thereof.

In some embodiments, the therapeutic cell population are on the surface of the scaffold at a density of between $1.3 \times 10^5$ cells/cm$^2$ and $2.95 \times 10^6$ cells/cm$^2$. In some embodiments, the therapeutic cell population are on the surface of the scaffold at a density of between $1.3 \times 10^5$ cells/cm$^2$ and $6 \times 10^6$ cells/cm$^2$. In some embodiments, the therapeutic cell population are on the surface of the scaffold at a density of between $2.9 \times 10^5$ cells/cm$^2$ and $5.5 \times 10^6$ cells/cm$^2$.

In some embodiments, the therapeutic cell population are of mammalian origin, such as human cells, canine cells, equine cells, feline cells, bovine cells, etc.

In some embodiments, the scaffold further comprises vasculature progenitor cells.

In some embodiments, the therapeutic cells are engineered to reduce or eliminate expression of CD40 and/or HLA or match HLA.

In some embodiments, the therapeutic cells are derived from inducible pluripotent stem cells (iPSCs) or embryonic stem cells.

In some embodiments, the scaffold is attached to the epicardium of the subject.

In some embodiments, the contacting comprises contacting the scaffold to the subject's left ventricle, right ventricle, left atrium, or right atrium.

In some embodiments, the therapeutic cells are proliferative at the time of contacting with the epicardium. In some embodiments, the therapeutic cells are non-proliferative at the time of contacting with the epicardium.

In some embodiments, the methods further comprise contacting the subject's heart with one or more of thymosin beta-4 (TB4), akt murine thymoma viral oncogene homolog (AKT1), stromal cell-derived factor-1 alpha (SDF-1), and hepatocyte growth factor (HGF) or other factors to influence cell growth, differentiation or migration/recruitment.

In some embodiments, the disorder or condition associated with aberrant cardiac tissue function is selected from the group consisting of ischemia-induced heart failure, chronic heart failure (CHF), ischemia without heart failure, cardiomyopathy, dilated cardiomyopathy (DCM), cardiac arrest, congestive heart failure, stable angina, unstable angina, myocardial infarction, coronary artery disease, valvular heart disease, ischemic heart disease, reduced ejection fraction, reduced myocardial perfusion, maladaptive cardiac remodeling, maladaptive left ventricle remodeling, reduced left ventricle function, left heart failure, right heart failure, backward heart failure, forward heart failure, systolic dysfunction, diastolic dysfunction, increased or decreased systemic vascular resistance, low-output heart failure, high-output heart failure, dyspnea on exertion, dyspnea at rest, orthopnea, tachypnea, paroxysmal nocturnal dyspnea, dizziness, confusion, cool extremities at rest, exercise intolerance, easy fatigue ability, peripheral edema, nocturia, ascites, hepatomegaly, pulmonary edema, cyanosis, laterally displaced apex beat, gallop rhythm, heart murmurs, parasternal heave, and pleural effusion.

In some embodiments, the treating comprises one or more of improving left ventricular function, decreasing left ventricular end diastolic pressure (EDP), improving myocardial perfusion, repopulating of the heart's wall with cardiomyocytes, reversing maladaptive left ventricle remodeling in CHF subjects, improvement in left ventricular passive filling, active filling, chamber compliance and parameters of heart failure including, but not limited to increasing E' (mm/s), decreasing E/E', increasing LV dP/dt (mmHg/sec) and decreasing Tau (msec).

In some embodiments, the material of the scaffold is synthetic, biological, degradable, non-degradable, porous, etc., which may include one or more of knitted, woven, bonded, spun, printed, degradable, non-degradable, allogeneic, autologous, xenograft, pores (even spacing, uneven spacing, varying sizes), extracellular matrix, etc.

In some embodiments, the scaffold is formed into a three-dimensional structure.

In some embodiments, the scaffold is a bio-absorbable mesh.

DETAILED DESCRIPTION

Figure 1:
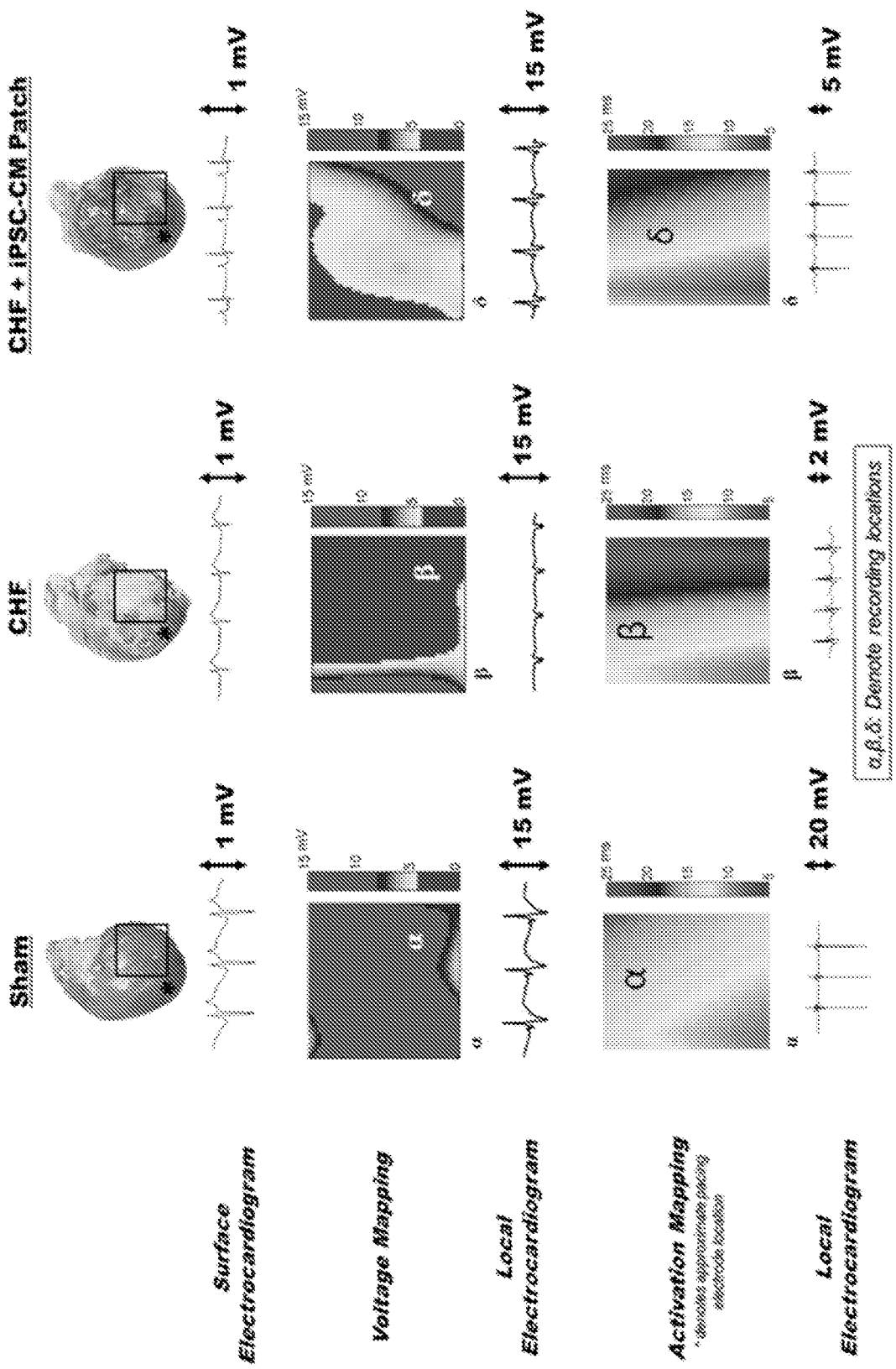
FIG. 1: In vivo electrophysiological analyses were performed to assess hiPSC-CM patch integration and electromechanical coupling to the host myocardium. Surface electrocardiogram (ECG), LV voltage map, local ECG and activation maps were collected from each group. Voltage mapping and activation mapping were performed using a custom engineered software program. Asterisks indicate the approximate epicardial pacing location for activation mapping only. Boxes on the Sham, CHF, and CHF+iPSC-CM patch hearts denote tissue region mapped to generate color maps for voltage and activation mapping. Greek letters denote focal area of local electrocardiograms from each group with respect to voltage or activation maps. Surface and local ECGs and voltage mapping are reported in millivolts. Activation mapping is reported in milliseconds. Implantation of the hiPSC-CM patch implants improve voltage amplitude and activation times across the previously infarct tissue.

As noted, experiments conducted during the course of developing embodiments for the present invention investigated the use of engineered grafts for improving cardiac function. Such experiments examined comparatively the therapeutic benefits of grafts alone, and grafts engineered with different therapeutic cells populations. Improved cardiac function outcome was demonstrated for each of grafts alone, and each of the grafts engineered with different therapeutic cells populations.

Accordingly, the present invention provides compositions and methods for improving cardiac function and/or treating cardiac tissue. For example, in some embodiments, the present invention provides scaffolds for improving cardiac function and/or treating cardiac tissue. In such embodiments, the provided scaffolds are adhered to a region of cardiac tissue (e.g., cardiac tissue of a subject (e.g., a mammalian subject) (e.g., a human subject)). In some embodiments, the cardiac tissue is epicardial tissue. In some embodiments, the cardiac tissue is endocardial tissue. In some embodiments, the cardiac tissue is cardiac tissue experiencing aberrant function (e.g., aberrant cardiac function). In some embodiments, the cardiac tissue is within the left ventricle, right ventricle, left atrium, right atrium, and/or multiple regions thereof.

Such embodiments are not limited to a specific type of scaffold. Indeed, the present invention contemplates the use of any suitable scaffold, including but not limited to any and all materials-synthetic, biological, degradable, non-degradable, porous, etc., which may include one or more of knitted, woven, bonded, spun, printed, degradable, non-degradable, allogeneic, autologous, xenograft, pores (even spacing, uneven spacing, varying sizes), extracellular matrix, etc.

In some embodiments, the scaffold is a substrate comprising a biocompatible, non-living material. Such scaffolds are not limited to a particular structure. In some embodiments, the scaffold is formed into a three-dimensional structure. In some embodiments, the scaffold is formed into a three-dimensional structure having interstitial spaces bridged by cells in the scaffold. In some embodiments, the scaffold is a bio-absorbable mesh. In some embodiments, the scaffold is configured for engagement and adherence with various types of living tissue (e.g., any type of cardiac tissue).

In some embodiments, the scaffold is a patch configured for application and adherence with a bodily tissue (e.g., cardiac tissue). As such, a cardiac scaffold or cardiac patch is any type or kind of patch is configured for attachment with heart tissue. Such a scaffold, patch, cardiac scaffold and cardiac patch can have additional cells or no additional cells.

The three-dimensional support framework fort the scaffold may be of any material and/or shape that: (a) allows cells to attach to it (or can be modified to allow cells to attach to it); and (b) allows cells to grow in more than one layer. A number of different materials may be used to form the framework, including but not limited to: proteins (e.g. collagen), carbohydrates, peptides, polyamides (e.g. nylon), polyesters (e.g. dacron), polystyrene, polypropylene, polyacrylates, polyvinyl compounds (e.g., polyvinylchloride; PVC), polycarbonate, polytetrafluorethylene (PTFE; TEFLON), thermanox (TPX), nitrocellulose, cotton, polyglycolic acid (PGA), cat gut sutures, cellulose, gelatin, dextran, etc. Any of these materials may be woven into a mesh to form the three-dimensional framework. Certain materials, such as nylon, polystyrene, etc., are poor substrates for cellular attachment. When these materials are used as the three-dimensional support framework, it is advisable to pre-treat the framework prior to inoculation of cells in order to enhance their attachment to the framework. For example, prior to inoculation with cells, nylon screens could be treated with 0.1 M acetic acid, and incubated in polylysine, fetal bovine serum, and/or collagen to coat the nylon. Polystyrene could be similarly treated using sulfuric acid.

When the construct is to be implanted directly in vivo, it may be preferable to use biodegradable scaffold materials such as peptides, PLA, PCL, PGA, catgut suture material, collagen, polylactic acid, or hyaluronic acid. For example, these materials may be woven into a three-dimensional framework such as a collagen sponge or collagen gel. Where the cultures are to be maintained for long periods of time or cryopreserved, non-degradable materials such as nylon, dacron, polystyrene, polyacrylates, polyvinyls, teflons, cotton, etc. may be preferred. A convenient nylon mesh which could be used in accordance with the invention is a nylon filtration mesh having an average pore size of 140 m and an average nylon fiber diameter of 90 m (#3-210/36, Tetko, Inc., N.Y.).

The construct can be contacted with the heart in any suitable way to promote attachment. The construct may be attached to various locations on the heart, including the epicardium, myocardium and endocardium, most preferably the epicardium. Means for attachment include, but are not limited to, direct adherence between the construct and the heart tissue, biological glue, suture, synthetic glue, laser dyes, or hydrogel. A number of commercially available hemostatic agents and sealants include SURGICAL® (oxidized cellulose), ACTIFOAM® (collagen), FIBRX® (light-activated fibrin sealant), BOHEAL® (fibrin sealant), FIBROCAPS® (dry powder fibrin sealant), polysaccharide polymers p-GlcNAc (SYVEC® patch; Marine Polymer Technologies), Polymer 27CK (Protein Polymer Tech.). Medical devices and apparatus for preparing autologous fibrin sealants from 120 ml of a patient's blood in the operating room in one and one-half hour are also known (e.g. Vivostat System).

In an alternative embodiment of the invention utilizing direct adherence, the construct is placed directly onto the heart and the product attaches via natural cellular attachment. In a further alternative embodiment, the construct is attached to the heart using surgical glue, preferably biological glue such as a fibrin glue. The use of fibrin glue as a surgical adhesive is well known. Fibrin glue compositions are known (e.g., see U.S. Pat. Nos. 4,414,971; 4,627,879 and 5,290,552) and the derived fibrin may be autologous (e.g., see U.S. Pat. No. 5,643,192). The glue compositions may also include additional components, such as liposomes containing one or more agent or drug (e.g., see U.S. Pat. Nos. 4,359,049 and 5,605,541) and include via injection (e.g., see U.S. Pat. No. 4,874,368) or by spraying (e.g., see U.S. Pat. Nos. 5,368,563 and 5,759,171). Kits are also available for applying fibrin glue compositions (e.g., see U.S. Pat. No. 5,318,524).

In another embodiment, a laser dye is applied to the heart, the construct, or both, and activated using a laser of the appropriate wavelength to adhere to the tissues. In alternative embodiments, the laser dye has an activation frequency in a range that does not alter tissue function or integrity. For instance, 800 nm light passes through tissues and red blood cells. Using indocyan green (ICG) as the laser dye, laser wavelengths that pass through tissue may be used. A solution of 5 mg/ml of ICG is painted onto the surface of the three-dimensional stromal tissue (or target site) and the ICG binds to the collagen of the tissue. A 5 ms pulse from a laser emitting light with a peak intensity near 800 nm is used to activate the laser dye, resulting in the denaturation of collagen which fuses elastin of the adjacent tissue to the modified surface.

In another embodiment, the construct is attached to the heart using a hydrogel. A number of natural and synthetic polymeric materials are sufficient for forming suitable hydrogel compositions. For example, polysaccharides, e.g., alginate, may be crosslinked with divalent cations, polyphosphazenes and polyacrylates are crosslinked ionically or by ultraviolet polymerization (U.S. Pat. No. 5,709,854). Alternatively, a synthetic surgical glue such as 2-octyl cyanoacrylate ("DERMABOND", Ethicon, Inc., Somerville, N.J.) may be used to attach the three-dimensional stromal tissue.

In an alternative embodiment of the present invention, the construct is secured to the heart using one or more sutures, including, but not limited to, 5-O, 6-O and 7-O proline sutures (Ethicon Cat. Nos. 8713H, 8714H and 8701H), poliglecaprone, polydioxanone, polyglactin or other suitable non-biodegradable or biodegradable suture material. When suturing, double armed needles are typically, although not necessarily, used.

As noted, experiments conducted during the course of developing embodiments for the present invention demonstrated improved cardiac function through adherence of a scaffold onto cardiac tissue. Such experiments further demonstrated improved cardiac function with scaffolds engineered with additional cell populations. In some embodiments, such scaffolds engineered with additional cell populations further comprise fibroblast cells. In some embodiments, scaffolds engineered with additional cell populations do not further comprise fibroblast cells.

Embodiments including scaffold having cells may be fetal or adult in origin, and may be derived from convenient sources such as skin, cardiac muscle, smooth muscle, skeletal muscle, liver, pancreas, brain, adipose tissue (fat) etc. Such tissues and or organs can be obtained by appropriate biopsy or upon autopsy. In some embodiments cells are human cells.

The cells may be of any desired type, including but not limited to muscle cells (skeletal muscle cells, smooth muscle cells, cardiac muscle cells such as cardiomyocyte) or progenitors thereof, endothelial progenitor cells, bone marrow cells, bone marrow cells, mesenchymal stem cells, umbilical cord blood cells or combinations thereof. Such cells can be isolated using standard techniques in the art, or may be obtained from commercial sources.

In some embodiments, the additional cell populations include stromal cells, including but not limited to, endothelial cells (see, e.g., U.S. Patent Application Publication No. 2009/0269316 and U.S. Pat. No. 4,963,489).

In some embodiments, the additional cell populations include therapeutic cells. Such embodiments are not limited to specific types of therapeutic cells. In some embodiments, the therapeutic cells can be derived from any source, including but not limited to fetal tissue, newborn tissue, adult tissues, derived from stem, progenitor cell populations, embryonic cells or reprogrammed somatic cells via induced pluripotent stem cells (iPSC) such as through viral, mRNA, episomal vectors etc. When the therapeutic cells are cardiac cells, the cardiac cells may be terminally differentiated cardiac cells, or may be non-terminally differentiated cells for a specific cardiac cell pathway, or combinations thereof. The cells may be from any suitable organism, such as mammalian, including but not limited to rodent, primate cells canine cells, equine cells, human cells. The cells can be derived from male or female subjects, or cells from male and female subjects can be combined.

In some embodiments, the therapeutic cells include fibroblasts, hiPSC-derived heterogeneous cardiac myocytes (hetCM), or cardiac progenitors (CPCs). In some embodiments, the therapeutic cells include a combination of fibroblasts with hetCM, VM, or CPC populations.

In some embodiments, the additional cells comprise cardiomyocytes and/or progenitors thereof such as cardiac stem cells. There are a limited number of intrinsic cardiac stem cells in the mature adult heart that are self-renewing, clonogenic, and multipotent, such that they differentiate into cardiomyocytes and, to a lesser extent, into smooth muscle and endothelial cells. Cardiac stem cells can be isolated and expanded in culture indefinitely. In one embodiment, the cardiac stem cells are characterized by cell surface markers: Lin−, c-Kit+, CD45−, CD34−.

In some embodiments, the additional cells include recombinant cells capable of expressing a gene product of interest for a given purpose. For example, in some embodiments, the additional cells include cardiomyocytes engineered to express one or more of thymosin beta-4 (TB4), akt murine thyoma viral oncogene homolog (AKT1), stroma cell-derived factor-1 alpha (SDF-1), and hepatocyte growth factor (HGF). Techniques for engineering cells to express a heterologus gene product are well known in the art, and utilize cell transfection by recombinant expression vector that operatively link a nucleic acid coding region or gene to any promoter capable of effecting expression of the gene product. Thus, in various embodiments, the additional cells comprise a recombinant expression vector encoding a nucleic acid sequence that encodes a polypeptide sequence. The promoter sequence used to drive expression of the disclosed nucleic acid sequences in a mammalian system may be constitutive (driven by any of a variety of promoters, including but not limited to, CMV, SV40, RSV, actin, EF, etc.) or inducible (driven by any of a number of inducible promoters including, but not limited to, tetracycline, ecdysone, steroid-responsive). See, for example, Sambrook, Fritsch, and Maniatis, in: Molecular Cloning, A Laboratory Manual, Cold Spring Harbor Laboratory Press, 1989; *Gene Transfer and Expression Protocols*, pp. 109-128, ed. E. J. Murray, The Humana Press Inc., Clifton, N.J.), and the Ambion 1998 Catalog (Ambion, Austin, TX).

In some embodiments, the scaffold is a three dimensional fibroblast construct (3DFC) comprising fibroblasts grown on a three-dimensional substrate comprising a biocompatible, non-living material formed into a three-dimensional structure having intersitial spaces bridged by the cells in the construct.

In some embodiments, the scaffold is a matrix cultured in vitro with human dermal construct of newborn dermal fibroblasts to produce living, metabolically active tissue. In such embodiments, the fibroblasts proliferate across the mesh and secrete a large variety of growth factors and cytokines, including human dermal collagen, fibronectin, and glycosaminoglycans (GAGs), embedding themselves in a self-produced dermal matrix. In culture the fibroblasts produce angiogenic growth factors: VEGF (vascular endothelial growth factor), HGF (hepatocyte growth factor), bFGF (basic fibroblast growth factor), and angiopoietin-1 (see, e.g., J. Anat. (2006) 209, pp 527-532).

In some embodiments, the scaffold comprises a patch with the additional cells and/or fibroblast cells on the top portion of the patch. In this embodiment, the top portion of the patch can be attached to a surface of interest, such as the heart. In other embodiments the cells are on bottom or on both sides of the patch.

In some embodiments, the scaffolds may be cultured and applied "fresh" or in some embodiments may be cryopreserved and thawed prior to application.

Contacting a scaffold (cultured with or without fibroblasts) with a suspension of cells to be seeded onto the scaffold can be done under any suitable conditions to facilitate application of the force that causes the cells to contact the scaffold, including but not limited to the conditions described below. In one alternative embodiment, the scaffold is placed in 0.1 to 5 ml of media (preferably 0.25 ml-2 ml, and more preferable 0.5 ml-1.0 ml of media), and cells are introduced in suspension, such that the volume of cell suspension is approximately double the volume of media in which the scaffold is placed. In one alternative embodiment that can be combined with any other embodiments herein, the contacting occurs at approximately 37° C. In a further alternative embodiment that can be combined with any other embodiments herein, the cell suspension has a concentration of at least $3 \times 10^6$ cells/ml where the cells to be seeded are contractile cells (such as cardiomyocytes or progrenitors thereof). In further alternative embodiments that can be combined with any other embodiments herein, the cell suspension has a concentration of at least $4 \times 10^6$ cells/ml and $5 \times 10^6$ cells/ml.

In one embodiment, each scaffold to be seeded is placed in a well so as to cover the base of the well and lay flat. The inventors have discovered that if the scaffold does not cover the base of the well (when seeding scaffolds placed in wells), a decreased retention of cells occurs, and results in an unequal distribution of cells across the patch due to cell bunching and clumping.

Subjecting the cells within the suspension to a force that causes said cells to contact the scaffold may comprise the use of any suitable force, including but not limited to a centrifugal force and an electrical force generated by an electric field, or combinations of such forces. In an alternative embodiment, a centrifugal force is used. The centrifugal force to be applied depends on a variety of factors, such as the cell type to be seeded onto the scaffold. In one alternative embodiment that can be combined with any other embodiments herein, the construct is centrifuged at between 1200 rpms and 1600 rpms for between 2 and 10 minutes. In an alternative embodiment, all constructs to be seeded are placed in a horizontal arrangement in wells (as opposed to vertical), so that each well is spun at the same radius.

In one alternative embodiment, the force may be applied within 0-300 seconds after contacting of the cell suspension with the scaffold in appropriate culture medium.

It will be understood by those of skill in the art that it is not a requirement that all cells in the suspension contact the scaffold as a result of the force application, as the cells can preferably be present in the suspension in an amount that saturates all available locations for seeding onto the scaffold. In one alternative embodiment, the seeded cells contact each other, such that multiple cell layers are provided on top of the scaffold. In embodiments where cardiomyocytes or precursors thereof are used, it is preferred that the seeded cells reside in the "valleys" between fibers on the scaffold.

Culturing the cells under conditions suitable for the cells to adhere to the scaffold may comprise the use of any culture media and conditions suitable for a given purpose, such as those in the examples that follow. Any useful media may be used, including but not limited to DMEM-LG supplemented with fetal bovine serum (5-15%; preferably 10%) and other appropriate factors (including but not limited to sodium bicarbonate and antibiotics. It will be understood by those of skill in the art that it is not a requirement that all cells in the suspension adhere to the scaffold as a result of the force application, as the cells can preferably be present in the suspension in an amount that saturates all available locations for adherence onto the scaffold. A basal medium such as RPMI 1640 or similar is used and supplemented with B27 or albumin or heparin or similar.

In some embodiments, the cells are adhered to the scaffold at a cell density ranging between $0.5 \times 10^6$ cells/cm$^2$ and $5 \times 10^6$ cells/cm$^2$ (e.g., between $1 \times 10^6$ cells/cm$^2$ and $4 \times 10^6$ cells/cm$^2$) (e.g., between $1.5 \times 10^6$ cells/cm$^2$ and $3 \times 10^6$ cells/cm$^2$).

In some embodiments, the scaffold comprises a patch, with the cells on the top portion of the patch. In this embodiment, the top portion of the patch can be attached to a surface of interest, such as the heart. In other embodiments the cells are on bottom or on both sides of the patch.

In some embodiments, the additional cells (e.g., therapeutic cells) are on the construct at a density of between $2 \times 10^5$ cells/cm$^2$ and $6 \times 10^6$ cells/cm$^2$. In another embodiment, the cardiac cells are on the construct at a density of between $2 \times 10^6$ cells/cm$^2$ and $6 \times 10^6$ cells/cm$^2$. In various further embodiments, the cardiac cells are on the construct at a density of between $2 \times 10^5$ cells/cm$^2$ and $5 \times 10^6$ cells/cm$^2$, $2 \times 10^5$ cells/cm$^2$ and $4 \times 10^6$ cells/cm$^2$, $2 \times 10^5$ cells/cm$^2$ and $3 \times 10^6$ cells/cm$^2$, $5 \times 10^5$ cells/cm$^2$ and $5 \times 10^6$ cells/cm$^2$, $5 \times 10^5$ cells/cm$^2$ and $4 \times 10^6$ cells/cm$^2$, $5 \times 10^5$ cells/cm$^2$ and $3 \times 10^6$ cells/cm$^2$, $1 \times 10^6$ cells/cm$^2$ and $5 \times 10^6$ cells/cm$^2$, $1 \times 10^6$ cells/cm$^2$ and $4 \times 10^6$ cells/cm$^2$, $1 \times 10^6$ cells/cm$^2$ and $3 \times 10^6$ cells/cm$^2$, $2 \times 10^5$ cells/cm$^2$ and $2.95 \times 10^6$ cells/cm$^2$; $5 \times 10^5$ cells/cm$^2$ and $2.95 \times 10^6$ cells/cm$^2$; $1 \times 10^6$ cells/cm$^2$ and $2.95 \times 10^6$ cells/cm$^2$; $1.5 \times 10^6$ cells/cm$^2$ and $2.95 \times 10^6$ cells/cm$^2$ $1.3 \times 10^5$ cells/cm$^2$ and $2.5 \times 10^6$ cells/cm$^2$; or $1.3 \times 10^5$ cells/cm$^2$ and $2 \times 10^6$ cells/cm$^2$.

In some embodiments, the additional cells (e.g., therapeutic cells) comprise a combination of non-terminally differentiated cells and terminally differentiated cells. In one such embodiment, the non-terminally differentiated cells and terminally differentiated cardiac cells are present on the construct in a ratio of between about 1:1 and about 50:1. In other embodiments, the ratio is between about 1:1 and about 40:1, about 1:1 and about 30:1, about 1:1 and about 20:1; about 1:1 and about 10:1, about 1:1 and about 5:1, or about 1:1 and about 1:2.

In a further embodiment, the therapeutic cells are engineered to reduce or eliminate expression of CD40 and/or HLA or match HLA. This embodiment provides cells that have been selected for a diminished immune profile, which would allow for better retention of the transplanted cells in the host, which is especially suitable for allogeneic transplantation.

In a further embodiment, the therapeutic cells are derived from inducible pluripotent stem cells (iPSCs) or embryonic stem cells. In non-limiting embodiments, the terminally differentiated cardiac cells may be generated on the construct using the methods of the invention described herein.

In one embodiment, the therapeutic cells comprise non-terminally differentiated cells. As used herein, an "non-terminally differentiated cells" lacks visible sarcomeres. In various embodiments, compared to "terminally differentiated cardiomyocytes", non-terminally differentiated cells possesses one or more of the following properties:

Morphologically smaller in cell size;
Decreased myofibril density;
Electrophysiologically stunted/diminished action potential amplitudes;
Reduced gene and/or protein expression of MYH7 (Beta myosin heavy chain), MYH6 (alpha myosin heavy chain), SCN5A, GJA1 (connexin 43), HCN4 (hyperpolarization-activated K+ channels), KCNJ2 (inward rectifier potassium ion channel), SERCA2a (sarcoendoplasmic reticulum ATPase), alpha actinin, cardiac troponin I (cTnI), Cardiac troponin T (cTnT).

In another embodiment, the therapeutic cells comprise terminally differentiated cardiomyocytes. As used herein, a "terminally differentiated cardiomyocytes" possess visible sarcomeres. In various embodiments, compared to "non-terminally differentiated cardiomyocytes," a terminally differentiated cardiomyocytes possesses one or more of the following properties:

Morphologically larger in cell size;
Increased myofibril density;
Electrophysiologically active action potential amplitudes;
Increased gene and/or protein expression of MYH7 (Beta myosin heavy chain), MYH6 (alpha myosin heavy chain), SCN5A, GJA1 (connexin 43), HCN4 (hyperpolarization-activated K+ channels), KCNJ2 (inward rectifier potassium ion channel), SERCA2a (sarcoendoplasmic reticulum ATPase), alpha actinin, cardiac troponin I (cTnI), Cardiac troponin T (cTnT).

In some embodiments, the non-terminally differentiated cells and/or the terminally differentiated cells cardiomyocytes are in or on the surface of the construct with fibroblasts (e.g., 3DFCS) at a density of between $1.3 \times 10^5$ cells/cm$^2$ and $6 \times 10^6$ cells/cm$^2$ and the cardiac cells are present in or on the surface of the 3DFCS in a ratio of between about 1:7 and about 50:1 with fibroblasts. In another embodiment, the non-terminally differentiated cardiomyocytes and/or the terminally differentiated cardiomyocytes are in or on the surface of the construct at a total density of between $1.2 \times 10^6$ cells/cm$^2$ and $4 \times 10^6$ cells/cm$^2$. In various embodiments, the construct comprises a dose range of cardiomyocytes at $2.9 \times 10^5$ cells/cm$^2$, $1.2 \times 10^6$ cells/cm$^2$ or $6 \times 10^6$ cells/cm$^2$ for therapeutic use. Cardiomyocyte populations may be 100% terminally differentiated cardiomyocyte or 100% non-terminally differentiated cells, 50% terminally differentiated cardiomyocytes and 50% non-terminally differentiated cells, or any suitable variation thereof.

In certain embodiments, such methods are used for treating subjects suffering from disorders or conditions associated with aberrant cardiac tissue function. In some embodiments, the subject is a mammal, most preferably a human.

Such methods are not limited to specific types or kinds of disorders or conditions associated with aberrant cardiac tissue function.

In some embodiments, the disorder or condition associated with aberrant cardiac tissue function is chronic heart failure (CHF). As used herein, "CHF" is a chronic (as opposed to rapid onset) impairment of the heart's ability to supply adequate blood to meet the body's needs. CHF may be caused by, but is distinct from, cardiac arrest, myocardial infarction, and cardiomyopathy. In one alternative embodiment, the subject suffers from congestive heart failure. In various further alternative embodiments that can be combined with any other embodiments herein, the subject's heart failure comprises left heart failure, right heart failure, backward heart failure (increased venous back pressure), forward heart failure (failure to supply adequate arterial perfusion), systolic dysfunction, diastolic dysfunction, systemic vascular resistance, low-output heart failure, high-output heart failure. In various further alternative embodiments that can be combined with any other embodiments herein, the subject's CHF may be any of Classes I-IV as per the New York Heart Association Functional Classification; more preferably Class III or IV.

Class I: no limitation is experienced in any activities; there are no symptoms from ordinary activities.
Class II: slight, mild limitation of activity; the patient is comfortable at rest or with mild exertion.
Class III: marked limitation of any activity; the patient is comfortable only at rest.
Class IV: any physical activity brings on discomfort and symptoms occur at rest.

In a further alternative embodiment that can be combined with any other embodiments herein, the subject has been diagnosed with CHF according to the New York Heart Association Functional Classification. In a further alternative embodiment that can be combined with any other embodiments herein, the subject is further characterized by one or more of the following: hypertension, obesity, cigarette smoking, diabetes, valvular heart disease, and ischemic heart disease.

In some embodiments, the disorder or condition associated with aberrant cardiac tissue function is a cardiac arrhythmia. As used herein a "cardiac arrhythmia" is an abnormal heart rhythm or rate, regardless of the cause.

In some embodiments, the cardiac arrhythmia is selected from the group consisting of tachycardia, bradycardia, ventricular tachycardia, ventricular fibrillation, arrhythmias generated from the upper chambers of the heart such as any supraventricular tacchycardia such as atrial fibrillation, and diseases of the atrioventricular nodal tissue such as complete heart block.

As used herein, "tachycardia" is an accelerated heart rate (i.e.: above 100 beats per minute). Supraventricular tachycardias include but is not limited to atrial fibrillation, atrial flutter, paroxysmal supraventricular tachycardia, paroxysmal atrial tachycardia, all supraventricular re-entry tachycardias, bypass tract tachycardias. Ventricular arrhythmias include ventricular fibrillation and ventricular tachycardia.

As used herein, "bradycardia" is a heart rate that is too slow (i.e.: below 60 beats per minute).

As used herein, "complete heart block" is a condition in which the impulse generated in the sinoatrial node (SA node) in the atrium of the heart does not propagate to the ventricles. This includes all forms of atria-ventricular (A-V) block, including but not limited to Wenckebach heart including Mobitz type I and type II block.

As used herein, "treat" or "treating" means accomplishing one or more of the following: (a) reducing the severity of the disorder (ex: treatment of Class IV subject to improve status to Class III for CHF subjects); (b) limiting or preventing development of symptoms characteristic of the disorder; (c) inhibiting worsening of symptoms characteristic of the disorder; (d) limiting or preventing recurrence of symptoms in patients that were previously symptomatic for the disorder. Signs characteristic of CHF include, but are not limited to reduced ejection fraction, reduced myocardial perfusion, maladaptive cardiac remodeling (such as left ventricle remodeling), reduced left ventricle function, dyspnea on exertion, dyspnea at rest, orthopnea, tachypnea, paroxysmal nocturnal dyspnea, dizziness, confusion, cool extremities at rest, exercise intolerance, easy fatigueability, peripheral edema, nocturia, ascites, hepatomegaly, pulmonary edema, cyanosis, laterally displaced apex beat, gallop rhythm, heart murmurs, parasternal heave, and pleural effusion.

In one embodiment, the constructs described herein find use in promoting the healing of ischemic heart tissue. The ability of the constructs to promote the healing of an ischemic tissue depends in part, on the severity of the ischemia. As will be appreciated by the skilled artisan, the severity of the ischemia depends, in part, on the length of time the tissue has been deprived of oxygen. Among such activities is the reduction or prevention of the remodeling of ischemic tissue. By "remodeling" herein is meant, the presence of one or more of the following: (1) a progressive thinning of the ischemic tissue, (2) a decrease in the number or blood vessels supplying the ischemic tissue, and/or (3) a blockage in one or more of the blood vessels supplying the ischemic tissue, and if the ischemic tissue comprises muscle tissue, (4) a decrease in the contractibility of the muscle tissue. Untreated, remodeling typically results in a weakening of the ischemic tissue such that it can no longer perform at the same level as the corresponding healthy tissue. Cardiovascular ischemia is generally a direct consequence of coronary artery disease, and is usually caused by rupture of an atherosclerotic plaque in a coronary artery, leading to formation of thrombus, which can occlude or obstruct a coronary artery, thereby depriving the downstream heart muscle of oxygen. Prolonged ischemia can lead to cell death or necrosis, and the region of dead tissue is commonly called an infarct.

In some embodiments, candidate subjects for the methods described herein will be patients suffering from disorders or conditions associated with aberrant cardiac tissue function.

In some embodiments, candidate subjects for the methods described herein will be patients with stable angina and reversible myocardial ischemia. Stable angina is characterized by constricting chest pain that occurs upon exertion or stress, and is relieved by rest or sublingual nitroglycerin. Coronary angiography of patients with stable angina usually reveals 50-70% obstruction of at least one coronary artery. Stable angina is usually diagnosed by the evaluation of clinical symptoms and ECG changes. Patients with stable angina may have transient ST segment abnormalities, but the sensitivity and specificity of these changes associated with stable angina are low.

In some embodiments, candidates for the methods described herein will be patients with unstable angina and reversible myocardial ischemia. Unstable angina is characterized by constricting chest pain at rest that is relieved by sublingual nitroglycerin. Anginal chest pain is usually relieved by sublingual nitroglycerin, and the pain usually subsides within 30 minutes. There are three classes of unstable angina severity: class I, characterized as new onset, severe, or accelerated angina; class II, subacute angina at rest characterized by increasing severity, duration, or requirement for nitroglycerin; and class III, characterized as acute angina at rest. Unstable angina represents the clinical state between stable angina and acute myocardial infarction (AMI) and is thought to be primarily due to the progression in the severity and extent of atherosclerosis, coronary artery spasm, or hemorrhage into non-occluding plaques with subsequent thrombotic occlusion. Coronary angiography of patients with unstable angina usually reveals 90% or greater obstruction of at least one coronary artery, resulting in an inability of oxygen supply to meet even baseline myocardial oxygen demand. Slow growth of stable atherosclerotic plaques or rupture of unstable atherosclerotic plaques with subsequent thrombus formation can cause unstable angina. Both of these causes result in critical narrowing of the coronary artery. Unstable angina is usually associated with atherosclerotic plaque rupture, platelet activation, and thrombus formation. Unstable angina is usually diagnosed by clinical symptoms, ECG changes, and changes in cardiac markers.

In some embodiments, candidates for the methods described herein will be human patients with left ventricular dysfunction and reversible myocardial ischemia that are undergoing a coronary artery bypass graft (CABG) procedure, who have at least one graftable coronary vessel and at least one coronary vessel not amenable to bypass or percutaneous coronary intervention.

In some embodiments, applications of the construct to an ischemic tissue increases the number of blood vessels present in the ischemic tissue, as measured using laser Doppler imaging (see, e.g., Newton et al., 2002, J Foot Ankle Surg, 41(4):233-7). In some embodiments, the number of blood vessels increases 1%, 2%, 5%; in other embodiments, the number of blood vessels increases 10%, 15%, 20%, even as much as 25%, 30%, 40%, 50%; in some embodiments, the number of blood vessels increase even more, with intermediate values permissible.

In some embodiments, application of the construct to an ischemic heart tissue increases the ejection fraction. In a healthy heart, the ejection fraction is about 65 to 95 percent. In a heart comprising ischemic tissue, the ejection fraction is, in some embodiments, about 20-40 percent. Accordingly, in some embodiments, treatment with the construct results in a 0.5 to 1 percent absolute improvement in the ejection fraction as compared to the ejection fraction prior to treatment. In other embodiments, treatment with the construct results in an absolute improvement in the ejection fraction more than 1 percent. In some embodiments, treatment results in an absolute improvement in the ejection fraction of 1.5%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, or more as compared to the ejection fraction prior to treatment. For example, if the ejection fraction prior to treatment was 40%, then following treatment ejection fractions between 41% to 59% or more are observed in these embodiments. In still other embodiments, treatment with the construct results in an improvement in the ejection fraction greater than 10% as compared to the ejection fraction prior to treatment.

In some embodiments, application of the construct to an ischemic heart tissue increases one or more of cardiac output (CO) (increases of up to 55% or more relative to pre-status treatment), left ventricular end diastolic volume index (LVEDVI), left ventricular end systolic volume index (LVESVI), and systolic wall thickening (SWT). These parameters are measured by art-standard clinical procedures, including, for example, nuclear scans, such as radionuclide ventriculography (RNV) or multiple gated acquisition (MUGA), and X-rays.

In some embodiments, application of the construct to an ischemic heart tissue causes a demonstrable improvement in the blood level of one or more protein markers used clinically as indicia of heart injury, such as creatine kinase (CK), serum glutamic oxalacetic transaminase (SGOT), lactic dehydrogenase (LDH) (see, e.g., U.S. Publication 2005/0142613), troponin I and troponin T can be used to diagnose heart muscle injury (see, e.g., U.S. Publication 2005/0021234). In yet other embodiments, alterations affecting the N-terminus of albumin can be measured (see, e.g., U.S. Publications 2005/0142613, 2005/0021234, and 2005/0004485; the disclosures of which are incorporated herein by reference in their entireties).

Additionally, the cultured three-dimensional tissue can be used with therapeutic devices used to treat heart disease including heart pumps, endovascular stents, endovascular stent grafts, left ventricular assist devices (LVADs), biventricular cardiac pacemakers, artificial hearts, and enhanced external counterpulsation (EECP).

In a further alternative embodiment that can be combined with any other embodiments herein, the treating results in production of new cardiomyocytes and new blood vessels in the subject. In a further alternative embodiment that can be combined with any other embodiments herein, the treating results in improvement of left ventricular function, fall in end diastolic pressure (EDP) (reduction of up to 50-60% or more relative to pre-status treatment), myocardial perfusion, repopulation of the anterior wall with cardiomyocytes, and/or reversing maladaptive left ventricle remodeling in the subject.

In one non-limiting alternative embodiment in which a synchronously beating construct is placed on the heart to aid in contraction of the left ventricle, beneficial treatment can be demonstrated by an improvement in ejection fraction. In a further non-limiting alternative embodiment, a non-beating construct is placed on the heart, then spontaneously begins beating on the heart to aid in contraction of the heart.

As used herein, the phrase "an amount effective" means an amount of the construct that will be effective to treat the disorder, as discussed herein. As will be clear to those of skill in the art, the methods comprise the use of one or more of the recited constructs to treat disorders characterized by a lack of functioning cardiomyocytes. In one embodiment, the method comprises contacting the heart with an amount of one or more constructs that serves to cover one or more ischemic regions of the heart, preferably all ischemic regions of the heart. The construct is used in an amount effective to promote tissue healing and/or revascularization of weakened or damaged heart tissue in an individual diagnosed with a disorder characterized by a lack of functioning cardiomyocytes. The amount of the construct administered, depends, in part, on the severity of the disorder, whether the construct is used as an injectable composition (see, US20060154365, incorporated herein by reference in its entirety), the concentration of the various growth factors and/or Wnt proteins present, the number of viable cells comprising the construct, and/or ease of access to the heart tissue(s) being treated. Determination of an effective dosage is well within the capabilities of those skilled in the art. Suitable animal models, such as the canine model described in US 20060292125 (incorporated by reference herein in its entirety) can be used for testing the efficacy of the dosage on a particular tissue of the heart.

As used herein "dose" refers to the number of cohesive pieces of construct applied to the heart of an individual diagnosed with congestive heart failure. A typical cohesive piece of construct is approximately 21.24 cm$^2$. As will be appreciated by those skilled in the art, the absolute dimensions of the cohesive piece can vary, as long it comprises a sufficient number of cells to promote healing of weakened or damaged heart tissue in an individual diagnosed with a disorder characterized by a lack of functioning cardiomyocytes. Thus, cohesive pieces suitable for use in the methods described herein can range in size from 15 cm$^2$ to 50 cm$^2$.

The application of more than one cohesive piece of construct can be used to increase the area of the heart treatable by the methods described herein. For example, in embodiments using a two pieces of cohesive construct, the treatable area is approximately doubled in size. In embodiments using three cohesive pieces of construct, the treatable area is approximately tripled in size. In embodiments using four cohesive pieces of construct, the treatable area is approximately quadrupled in size. In embodiments using five cohesive pieces of construct, the treatable area is approximately five-fold, i.e. from 21.24 cm$^2$ to 175 cm$^2$.

In some embodiments, one cohesive piece of construct is attached to a region of the heart in an individual diagnosed with a disorder characterized by a lack of functioning cardiomyocytes.

In other embodiments, two cohesive pieces of construct are attached to a region of the heart in an individual diagnosed with a disorder characterized by a lack of functioning cardiomyocytes.

In other embodiments, three cohesive pieces of construct are attached to a region of the heart in an individual diagnosed with a disorder characterized by a lack of functioning cardiomyocytes.

In other embodiments, four, five, or more cohesive pieces of construct are attached to a region of the heart in an individual diagnosed with a disorder characterized by a lack of functioning cardiomyocytes.

In embodiments in which two or more cohesive pieces of construct are administered, the proximity of one piece to another can be adjusted, depending in part on, the severity of the disorder characterized by a lack of functioning cardiomyocytes, the extent of the area being treated, and/or ease of access to the heart tissue(s) being treated. For example, in some embodiments, the pieces of construct can be located immediately adjacent to each other, such that one or more edges of one piece contact one or more edges of a second piece. In other embodiments, the pieces can be attached to the heart tissue such that the edges of one piece do not touch the edges of another piece. In these embodiments, the pieces can be separated from each other by an appropriate distance based on the anatomical and/or disease conditions presented by the subject. Determination of the proximity of one piece to another, is well within the capabilities of those skilled in the art, and if desired can be tested using suitable animal models, such as the canine model described in US20060292125.

In embodiments that comprise a plurality of pieces of construct, some, or all of the pieces can be attached to the same or different areas of the heart.

In embodiments that comprise a plurality of pieces of construct, the pieces are simultaneously attached, or concurrently attached to the heart.

In some embodiments, the construct pieces are administered over time. The frequency and interval of administration depends, in part, on the severity of the disorder, whether the construce is used as an injectable composition (see, US20060154365, incorporated herein by reference in its entirety), the concentration of the various growth factors and/or Wnt proteins present, the number of viable cells comprising the scaffold, and/or ease of access to the heart tissue(s) being treated. Determination of the frequency of administration and the duration between successive applications is well within the capabilities of those skilled in the art, and if desired, can be tested using suitable animal models, such as the canine model described in US20060292125.

In a further alternative embodiment, one or more construct is contacted with the left ventricle. In a further alternative embodiment, the one or more constructs cover the entire heart.

In embodiments that comprise a plurality of pieces of construct, some, or all of the pieces can be attached to the area comprising the heart. In other embodiments, one or more of the construct pieces can be attached to areas that do not comprise damaged myocardium. For example, in some embodiments, one piece can be attached to an area comprising ischemic tissue and a second piece can be attached to an adjacent area that does not comprise ischemic tissue. In these embodiments, the adjacent area can comprise damaged or defective tissue. "Damaged," or "defective" tissue as used herein refer to abnormal conditions in a tissue that can be caused by internal and/or external events, including, but not limited to, the event that initiated the ischemic tissue. Other events that can result in ischemic, damaged or defective tissue include disease, surgery, environmental exposure, injury, aging, and/or combinations thereof.

In embodiments that comprise a plurality of pieces of cultured three-dimensional tissue, the construct pieces can be simultaneously attached, or concurrently attached to an ischemic tissue.

The methods and compositions described herein can be used in combination with conventional treatments, such as the administration of various pharmaceutical agents and surgical procedures. For example, in some embodiments, the cultured three-dimensional tissue is administered with one or more of the medications used to treat a disorder characterized by a lack of functioning cardiomyocytes. Medications suitable for use in the methods described herein include angiotensin-converting enzyme (ACE) inhibitors (e.g., enalapril, lisinopril, and captopril), angiotensin II (A-II) receptor blockers (e.g., losartan and valsartan), diuretics (e.g., bumetanide, furosemide, and spironolactone), digoxin, beta blockers, and nesiritide.

Additionally, the constructs can be used with other options used to treat a disorder characterized by a lack of functioning cardiomyocytes, including heart pumps, also referred to as left ventricular assist devices (LVADs), biventricular cardiac pacemakers, cardiac wrap surgery, artificial hearts, and enhanced external counterpulsation (EECP), and cardiac wrap surgery (see, e.g., U.S. Pat. Nos. 6,425,856, 6,085,754, 6,572,533, and 6,730,016, the contents of which are incorporated herein by reference).

In some embodiments, the construct is used in conjunction with cardiac wrap surgery. In these embodiments, a flexible pouch or jacket is used to deliver and/or attach the construct, which can be placed inside or embedded within the pouch prior to placement over the damaged or weakened heart tissue. In other embodiments, the pouch and the 3DFC can be joined together. For example, the pouch and the construct can be joined together using a stretchable stitch assembly. In other embodiments, the construct can be configured to comprise threads useful for joining the framework to the pouch. U.S. Pat. Nos. 6,416,459, 5,702,343, 6,077,218, 6,126,590, 6,155,972, 6,241,654, 6,425,856, 6,230,714, 6,241,654, 6,155,972, 6,293,906, 6,425,856, 6,085,754, 6,572,533, and 6,730,016 and U.S. Patent Publication Nos. 2003/0229265, and 2003/0229261, the contents of which are incorporated herein by reference, describe various embodiments of pouches and jackets, e.g., cardiac constraint devices, that can be used to deliver and/or attach the construct.

In some embodiments, other devices, in addition to the construct are attached to the pouch, e.g., electrodes for defibrillation, a tension indicator for indicating when the jacket is adjusted on the heart to a desired degree of tensioning, and used in the methods and compositions described herein. See, e.g., U.S. Pat. Nos. 6,169,922 and 6,174,279, the contents of which are incorporated herein by reference.

A number of methods can be used to measure changes in the functioning of the heart in subjects before and after attachment of the construct. For example, an echocardiogram can be used to determine the capacity at which the heart is pumping. The percentage of blood pumped out of the left ventricle with each heartbeat is referred to as the ejection fraction. In a healthy heart, the ejection fraction is about 60 percent. In an individual with chronic heart failure caused by the inability of the left ventricle to contract vigorously, i.e., systolic heart failure, the ejection fraction is usually less than 40 percent. Depending on the severity and cause of the heart failure, ejection fractions typically range from less than 40 percent to 15 percent or less. An echocardiogram can also be used to distinguish between systolic heart failure and diastolic heart failure, in which the pumping function is normal but the heart is stiff.

In some embodiments, echocardiograms are used to compare the ejection fractions before and following treatment with the construct. In certain embodiments, treatment with the construct results in improvements in the ejection fraction between 3 to 5 percent. In other embodiments, treatment with the construct results in improvements in the ejection fraction between 5 to 10 percent. In still other embodiments, treatment with the construct results in improvements in the ejection fraction greater than 10 percent.

Nuclear scans, such as radionuclide ventriculography (RNV) or multiple gated acquisition (MUGA) scanning can be used to determine how much blood the heart pumps with each beat. These tests are done using a small amount of dye injected in the veins of an individual A special camera is used to detect the radioactive material as it flows through the heart. Other tests include X-rays and blood tests. Chest X-rays can be used to determine the size of the heart and if fluid has accumulated in the lungs. Blood tests can be used to check for a specific indicator of congestive heart failure, brain natriuretic peptide (BNP). BNP is secreted by the heart in high levels when it is overworked. Thus, changes in the level of BNP in the blood can be used to monitor the efficacy of the treatment regime.

In a further aspect, the present invention provides kits for treating disorders or conditions associated with aberrant cardiac tissue function, comprising a suitable construct as disclosed above and a means for attaching the construct to the heart or organ. The means for attachment may include any such attachment device as described above, for example, a composition of surgical glue, hydrogel, or preloaded prolene needles for microsuturing.

EXPERIMENTAL

Experiments were performed evaluating improvements in the electrical function of treated cardiac tissue. Specifically, voltage properties, programmed electrical stimulation (PES) and action potential duration (APD) were studied.

Millivoltage measurements reflect how much voltage a tissue can generate with higher voltages representing healthier tissue. Programmed electrical stimulation is a technique used to study the heart's susceptibility for potentially lethal arrhythmias, specifically PES is used to induce ventricular tacchycardia (VT) to determine the patient's or animal's susceptibility to have a life threatening ventricular arrhythmia, i.e., VT or ventricular fibrillation (VF). Heart tissue that is easily induced into an arrhythmia, but specifically VT, indicates diseased tissue. Action potential duration measures how long it takes an electrical impulse to move through tissue. The longer the duration, the more diseased the tissue.

Improvements in millivoltage amplitude after implantation of the patch was demonstrated. These improvements could be mediated through a number of different mechanisms either independently or taken together such as but not limited to 1) conduction through the biomaterial (ie, biomaterial is conductive), 2) the cells integrate into the host tissue (permanently or transiently), 3) the patch induces endogenous repair of the tissue, or 4) increasing cell/tissue mass (with or without cardiomyocytes) in the previously injured tissue occurs. Implantation of a patch also reduced the susceptibility of induction of VT during PES and decreased the action potential duration meaning an improvement in speed of electrical activity through the infarcted area of the heart. Such results indicate, patches of the invention globally improves electrical function in the heart.

For these experiments numerous groups were tested. Sham and CHF controls were performed in addition to mesh alone, mesh with fibroblasts or mesh with fibroblast and of the following different induced pluripotent stem cell (iPSC) derived mesoderm lineage cell:terminally differentiated heterogenous CMs (HetCMs), ventricular pure (VM) CMs and cardiac progenitors (CPCs). All treatment groups showed an improvement in electrical function/performance of the heart.

Along with other functional benefits which include but are not limited to improved systolic function, improved diastolic function, and attenuation of maladaptive cardiac remodeling, the cardiac patches can be used to treat electrical pathologies in diseased heart tissue. These include acquired or congenital pathologies such as but are not limited to ventricular arrhythmias, such as ventricular tachycardia, ventricular fibrillation and supraventricular arrhythmias such as arrhythmias generated from the atria or upper chambers of the heart such as atrial fibrillation, and diseases of the atrioventricular nodal tissue such as any degree of atria-ventricular (A-V) block including complete heart block. The cardiac patch could be a biologic treatment for these indications and would challenge the current clinical standard of using implantable defibrillators, pacemakers and ablation treatments to treat arrhythmias. These cardiac patch preparations may be used independently or in conjunction with current standard of care.

FIG. 1 shows electrophysiology methods of determining in vivo voltage amplitudes, conduction velocity, ventricular tachycardia (VT) susceptibility.

TABLE 1

Suseptability of sustained ventricular tachycardia (sVT) was determined in rats treated with each candidate cell population and mesh alone. At the terminal portion of the study rats were subjected to programmed electircal stimulation in an effort to induce sVT. This protocol results in a 72% increase in suseptabiliyt of chronic heart failure (CHF) animals to go into sVT as compared to sham operated animals, of which 0% developed sVT. Treatement of rats with patches generated with mesh alone, mesh + fibroblasts, mesh + fibroblast + heterogeneous (HetCM), mesh + fibroblasts + ventricualr pure (VM) cardiomyocytes, mesh + fibroblasts + cardiac progentior cells (CPCs) resulted in a decreases suseptability of sVT. Sustained VT (sVT) is defined by having greater than 15 premature ventricular contractions (PVCs).

| Population | N | Fraction of induced sVT (>15 PVCs) | ERP Mean Range (milli-seconds) | Ejection Fraction (EF) % | End diastolic pressure (EDP) mmHg |
|---|---|---|---|---|---|
| Sham | 15 | 0/15 (05) | 54 ± 4 | 76 ± 3 | 6 ± 1φ |
| CHF | 29 | 21/29 (72%)* | 69 ± 3 | 34 ± 2 | 20 ± 2 |
| Mesh Only in CHF | 5 | 2/5 (40%) | 97 ± 9 #@ | 39 ± 11 | 23 ± 6 |
| Mesh + Fibroblasts in CHF | 12 | 5/12 (42%)* | 88 ± 7 #@ | 40 ± 5† | 21 ± 3 |
| Mesh + Fibroblasts + HetCM in CHF | 4 | 1/4 (25%) | 77 ± 3 | 32 ± 4 | 12 ± 1φ |
| Mesh + Fibroblasts + VM in CHF | 3 | 1/3 (33%) | 60 ± 18 | 42 ± 4† | 12 ± 3φ |
| Mesh + Fibroblasts + Cardiac Progenitors | 10 | 4/10 (40%) | 73 ± 5 | 44 ± 4† | 13 ± 5φ |

Table 1 Legend:
Data are presented as Mean ± Standard Error.
Sham n = 15,
CHF n = 29,
Mesh Only n = 5,
Mesh + Fibroblasts n = 12,
Mesh + fibrobalsts + HetCM CM n = 4,
Mesh + Fibroblasts + VM CMs n = 3,
Mesh + Fibrobalsts + CPCs.
Abbreviations: HetCm = heterogenous cardiomyocytes,
VM = ventricular myocytes,
CPC = cardiac progenitors,
CHF = Chronic heart failure,
sVT = sustained ventricular tachycardia,
ERP = effective refractory period,
PVC = Pre ventricualr contractions,
EF = ejection fraction,
EDP = end diastolic pressure.
Fraction of Induced Sustained Ventricular Tachycardia statistical analysis was performed using two-tailed Chi Squared with Yates Correction with the significance level at 0.05.
*denotes statistically significant difference versus 'SHAM'. Effective Refractory Period Mean statistical analysis was performed using One Way Analysis of Variance (ANOVA) with subsequent Holm-Sidak Test with the significance level at 0.05.
sign denotes statistically significant difference versus 'SHAM'.
@ denotes statistically significant difference versus 'CHF'.
Ejection Fraction Mean statistical analysis was performed using One Way Analysis of Variance (ANOVA) with subsequent Holm-Sidak Test with the significance level at 0.05.
†sign denotes statistically significant difference versus 'SHAM'.
End Diastolic Pressure Mean statistical analysis was performed using One Way Analysis of Variance (ANOVA) with subsequent Holm-Sidak Test with the significance level at 0.05.
φdenotes statistically significant difference versus 'SHAM'.

Cardiac grafts were generated with hetCMs, VMs or CPCs by co-culture into a 3D bio-absorbable mesh with human dermal fibroblasts. The hetCMs contain 60% ventricular, 40% atrial and nodal-like cardiomyocytes. The VMs contain 90% ventricular and 10% atrial cardiomyocytes. Grafts were evaluated in culture out to 6 days.

Figure 2:
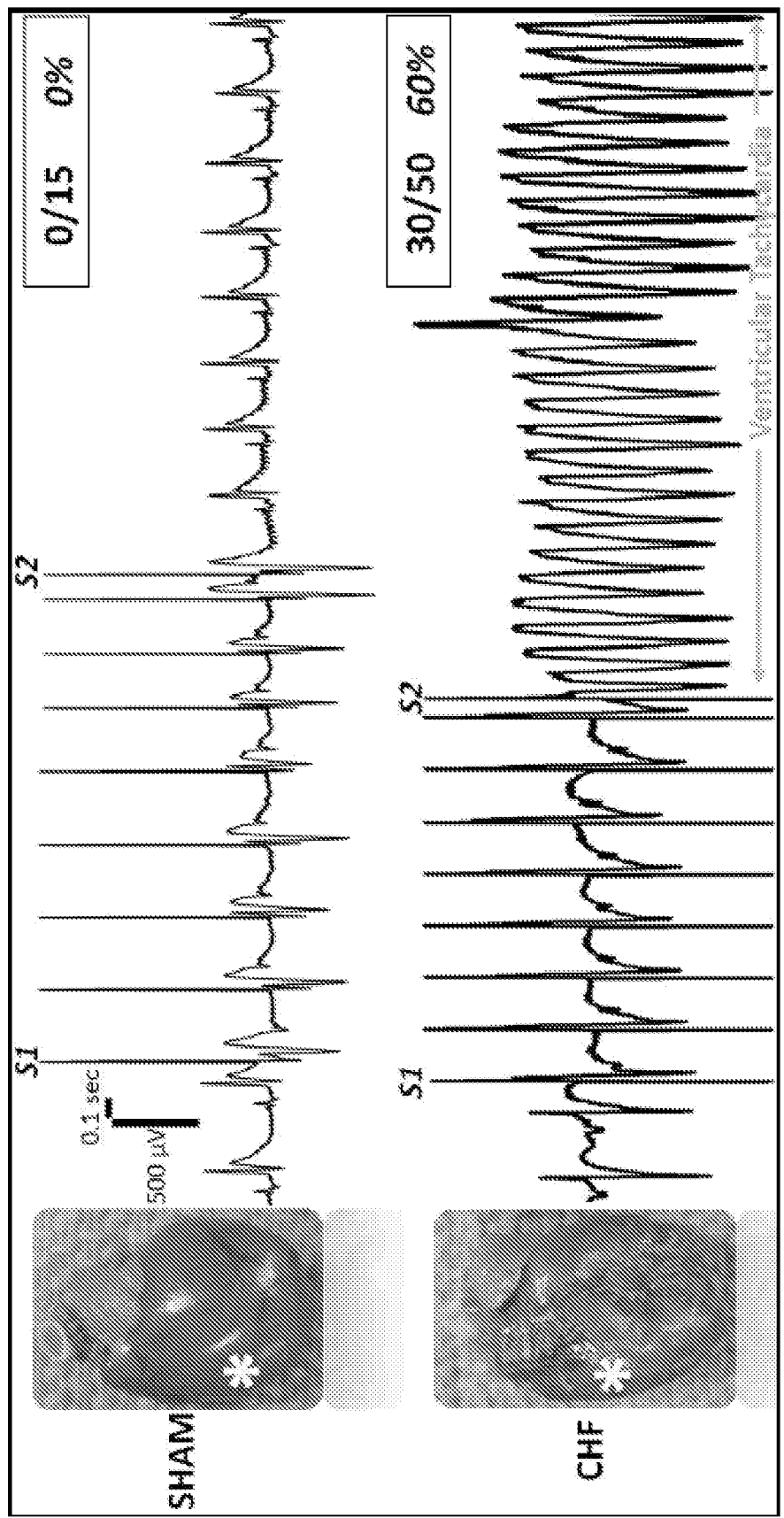
FIG. 2: Sample ECGs with fraction of inducible animals. Each strip begins with sinus rhythm. These groups served as controls for evaluation of the arrhythmogenic qualities of the hetCM and VM grafts. * indicates approximate location of the pacing electrodes.

Adult male Sprague-Dawley rats underwent permanent left coronary artery ligation and were randomized to SHAM, CHF, or graft treatment. Left ventricle (LV) hemodynamic measurements and ventricular tachycardia (VT) induction studies were performed 3 weeks post-implant (6 weeks post-ligation) using methods developed in the laboratory. We have defined sustained VT as greater than 15 consecutive premature ventricular contractions (PVCs) (FIG. 2).

Figure 3:
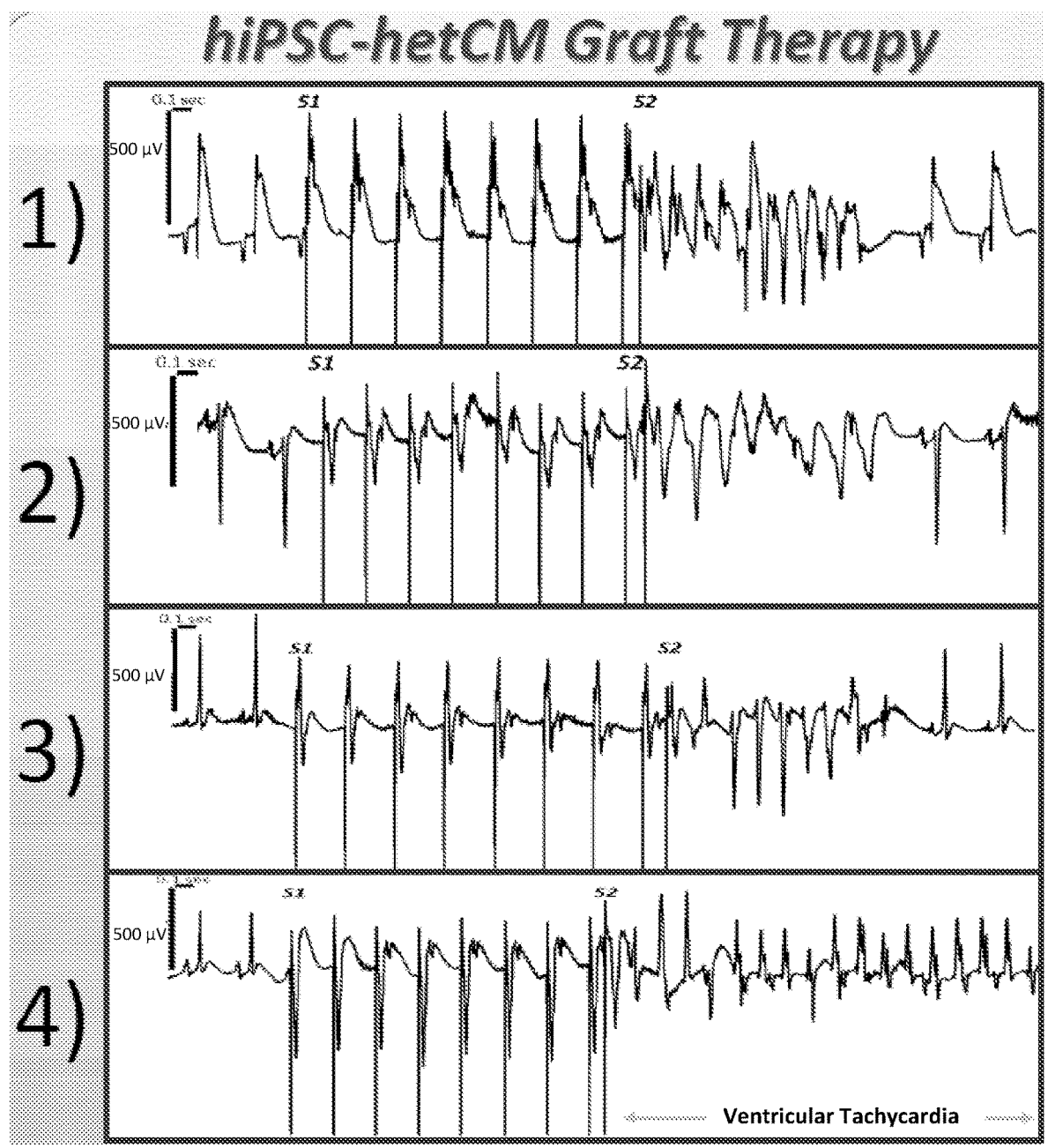
FIG. 3: ECGs from each of the four rats treated with hiPSC-hetCM cardiac grafts. One of four rats (25%) experience sustained ventricular tachycardia. Each strip begins with sinus rhythm.
Figure 4:
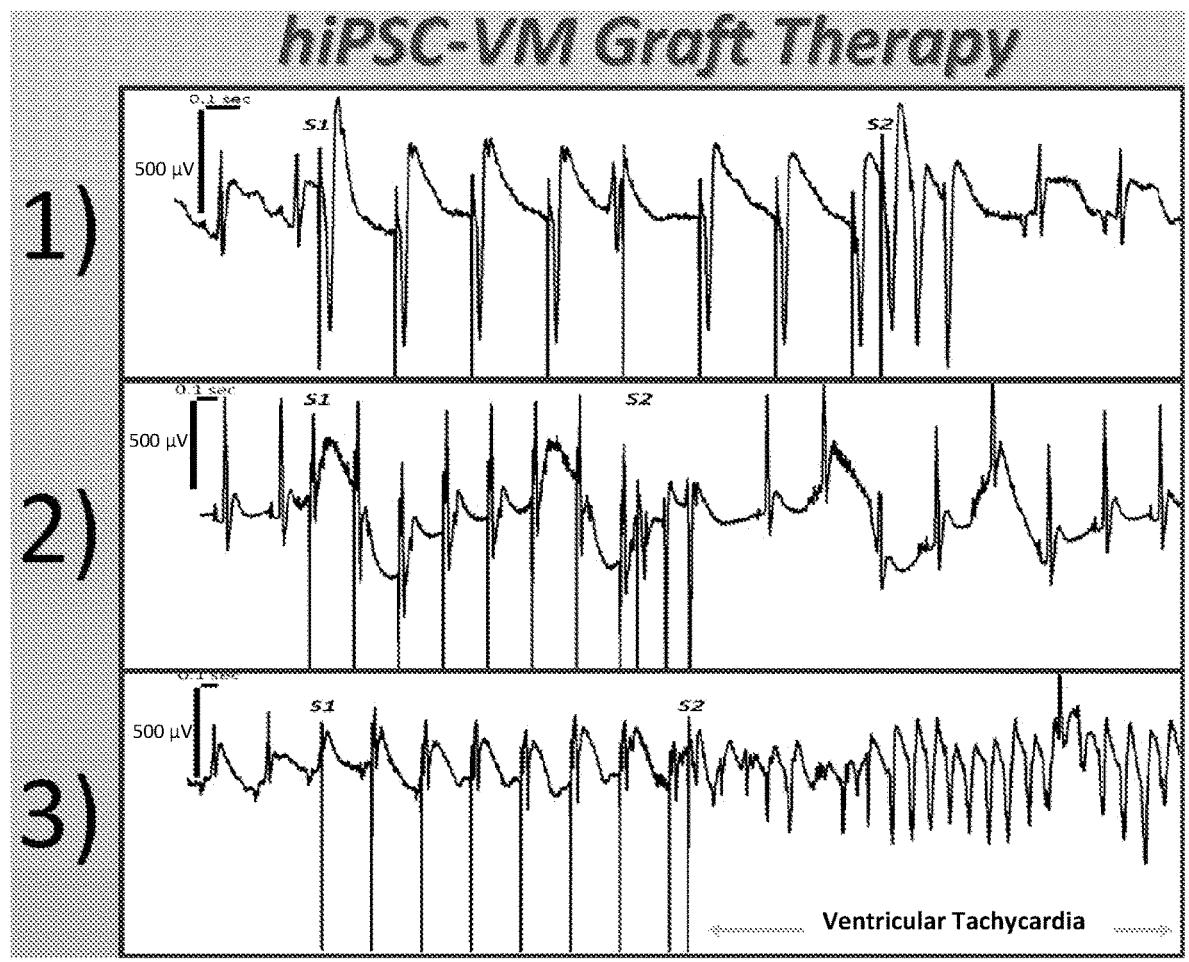
FIG. 4: ECGs from each of the three rats treated with hiPSC-VM cardiac grafts. One of three rats (33%) experience sustained ventricular tachycardia. Each strip begins with sinus rhythm.

Both hetCM and VM-derived cardiac grafts displayed synchronous and spontaneous contractions after 48 hrs in culture and maintained an average contraction rate (±Standard Error of Mean) of 67±6 and 71±9 beats per minute, respectively (n=10 per group). Cardiac progenitor cells grafts did not spontaneously contract. Implantation of hetCM VM, CPC grafts improved (p<0.05) left ventricular end diastolic pressure (EDP) by 40%, 40% and 35% respectively and resulted in decreased susceptibility to VT induction by 65%, 54% and 44% respectively (Table 1, FIGS. 3.&4).

Cardiac grafts engineered with hetCMs, VMs or CPCs and implanted in a rat CHF model can lower LV EDP in-vivo while decreasing susceptibility of induced VT. This approach raises the possibility that hiPSC-derived engineered cardiac grafts may be used as a treatment for VT in patients with CHF. These data also support that grafts alone (without cells) or with fibroblasts only may also have therapeutic potential as a treatment for VT in patients with CHF.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within

We claim:

1. A method for treating a subject having a disorder or condition associated with aberrant cardiac tissue function, comprising
   contacting a heart of a patient having a disorder or condition associated with aberrant cardiac tissue function with an engineered cardiac graft comprising one or more therapeutic cell populations associated with a scaffold,
   wherein the one or more cell populations comprises human induced pluripotent stem cell (hiPSC)-derived heterogeneous cardiac myocytes (hetCM),
   wherein the hetCM comprise a mixture of ventricular, atrial, and nodal cardiomyocytes,
   wherein the hetCM comprise 50%-90% ventricular cardiomyocytes, and 10%-50% atrial and nodal cardiomyocytes,
   wherein the scaffold is a substrate comprising a biocompatible, non-living material.

2. The method of claim 1, wherein the disorder or condition associated with aberrant cardiac tissue function is a cardiac arrhythmia.

3. The method of claim 2, wherein the cardia arrhythmia is selected from the group consisting of tachycardia, bradycardia, ventricular tachycardia, ventricular fibrillation, arrhythmias generated from the upper chambers of the heart, supraventricular tachycardia, atrial fibrillation, diseases of the atrioventricular nodal tissue, and complete heart block.

4. The method of claim 1,
wherein the one or more therapeutic cell populations are on the scaffold at a density of between $1.3 \times 10^5$ cells/$cm^2$ and $6 \times 10^6$ cells/$cm^2$, and/or
wherein the one or more therapeutic cell populations are of mammalian origin selected from human cells, canine cells, equine cells, feline cells, and bovine cells.

5. The method of claim 1, wherein the scaffold further comprises vasculature progenitor cells.

6. The method of claim 1, wherein the one or more therapeutic cell populations are engineered to reduce or eliminate expression of CD40 and/or HLA and/or match HLA.

7. The method of claim 1, further comprising contacting the subject's heart with one or more of thymosin beta-4 (TB4), akt murine thymoma viral oncogene homolog (AKT1), stromal cell-derived factor-1 alpha (SDF-1), and hepatocyte growth factor (HGF).

8. The method of claim 1, wherein the disorder or condition associated with aberrant cardiac tissue function is selected from the group consisting of ischemia-induced heart failure, chronic heart failure (CHF), ischemia without heart failure, cardiomyopathy, dilated cardiomyopathy (DCM), cardiac arrest, congestive heart failure, stable angina, unstable angina, myocardial infarction, coronary artery disease, valvular heart disease, ischemic heart disease, reduced ejection fraction, reduced myocardial perfusion, maladaptive cardiac remodeling, maladaptive left ventricle remodeling, reduced left ventricle function, left heart failure, right heart failure, backward heart failure, forward heart failure, systolic dysfunction, diastolic dysfunction, increased or decreased systemic vascular resistance, low-output heart failure, high-output heart failure, dyspnea on exertion, dyspnea at rest, orthopnea, tachypnea, paroxysmal nocturnal dyspnea, dizziness, confusion, cool extremities at rest, exercise intolerance, easy fatigue ability, peripheral edema, nocturia, ascites, hepatomegaly, pulmonary edema, cyanosis, laterally displaced apex beat, gallop rhythm, heart murmurs, parasternal heave, and pleural effusion.

9. The method of claim 1, wherein the treating comprises one or more of improving conduction speed, improving conduction amplitude, reducing aberrant beats, improving left ventricular function, decreasing left ventricular end diastolic pressure (EDP), improving myocardial perfusion, repopulating of the heart's wall with cardiomyocytes, reversing maladaptive left ventricle remodeling in CHF subjects, improvement in left ventricular passive filling, active filling, chamber compliance and parameters of heart failure selected from increasing E' (mm/s), decreasing E/E', increasing LV dP/dt (mmHg/sec), and decreasing Tau (msec).

10. The method of claim 1,
wherein the material of the scaffold is synthetic or biological,
wherein the material of the scaffold is degradable or non-degradable, and/or
wherein the material of the scaffold is porous or non-porous.

11. The method of claim 1, wherein the scaffold is a bio-absorbable mesh.

* * * * *